(12) United States Patent
Theobald

(10) Patent No.: US 9,393,692 B1
(45) Date of Patent: Jul. 19, 2016

(54) APPARATUS AND METHOD OF ASSISTING AN UNATTENDED ROBOT

(71) Applicant: Daniel Theobald, Somerville, MA (US)

(72) Inventor: Daniel Theobald, Somerville, MA (US)

( * ) Notice: Subject to any disclaimer, the term of this patent is extended or adjusted under 35 U.S.C. 154(b) by 144 days.

(21) Appl. No.: 13/952,713

(22) Filed: Jul. 29, 2013

(51) Int. Cl.
*B25J 9/16* (2006.01)
*B25J 5/00* (2006.01)

(52) U.S. Cl.
CPC *B25J 9/1666* (2013.01); *B25J 5/00* (2013.01); *Y10S 901/01* (2013.01)

(58) Field of Classification Search
CPC .......... B25J 9/1666; B25J 5/00; Y10S 901/01
USPC .......................................................... 701/28
See application file for complete search history.

(56) References Cited

U.S. PATENT DOCUMENTS

| | | | |
|---|---|---|---|
| 8,447,474 B2* | 5/2013 | Breed | A01C 7/102 180/169 |
| 2007/0192910 A1* | 8/2007 | Vu et al. | 901/17 |
| 2007/0197889 A1* | 8/2007 | Brister et al. | 600/347 |
| 2007/0276270 A1* | 11/2007 | Tran | 600/508 |
| 2010/0036393 A1* | 2/2010 | Unsworth | 606/130 |
| 2011/0216179 A1* | 9/2011 | Dialameh et al. | 348/62 |
| 2012/0101952 A1* | 4/2012 | Raleigh et al. | 705/304 |
| 2012/0326917 A1* | 12/2012 | Kiehne | B60T 7/22 342/71 |

* cited by examiner

*Primary Examiner* — McDieunel Marc
*Assistant Examiner* — James E Stroud
(74) *Attorney, Agent, or Firm* — Albert J. Brunett

(57) ABSTRACT

A method of controlling a robot, receives a first message from an unattended robot relating to movement of the robot. Receipt of the first message indicates that movement of the robot is impeded by an environmental condition. The method then determines how to correct the impeded movement caused by the environmental condition, and forwards a second message toward the robot having correction information, which enables the robot to move without impediment by the environmental condition.

6 Claims, 5 Drawing Sheets

APPARATUS AND METHOD OF ASSISTING AN UNATTENDED ROBOT

FIELD OF THE INVENTION

The present invention relates generally to robotics and, in at least one embodiment, to systems and methods of assisting unattended robots.

BACKGROUND OF THE INVENTION

Movable autonomous robots are used in a growing number of applications. For example, autonomous robots now are used in hospitals both to minimize provider burden, and improve the patient experience. Among other things, such robots can deliver food or medicine to patients, or help patients to the restroom. Some currently available robots, such as the QCBOT robot, distributed by Vecna Technologies, Inc. of Cambridge, Mass., serves as an automated materials transport and delivery device, while providing mobile patient self-service, such as check-in, bedside registration, and wayfinding.

Autonomous robots can use machine vision and computer learning technologies to navigate within their environments. Problems can arise, however, when the robots cannot discern or recognize an environmental condition (e.g., a dog or a large white wall) within their local environments. For example, some autonomous robots may stop moving when they cannot discern some environmental condition.

SUMMARY OF THE INVENTION

In accordance with one embodiment of the invention, a method of controlling a robot, receives a first message from an unattended robot relating to movement of the robot. Receipt of the first message indicates that movement of the robot is impeded by an environmental condition. The method then determines how to correct the impeded movement caused by the environmental condition, and forwards a second message toward the robot having correction information, which enables the robot to move without impediment by the environmental condition.

BRIEF DESCRIPTION OF THE DRAWINGS

The following detailed description will be better understood when read in conjunction with the appended drawings in which there is shown one or more of the multiple embodiments of the present disclosure. It should be understood, however, that the various embodiments of the present disclosure are not limited to the precise arrangements and instrumentalities shown in the drawings.

DETAILED DESCRIPTION OF THE INVENTION

Figure 1:
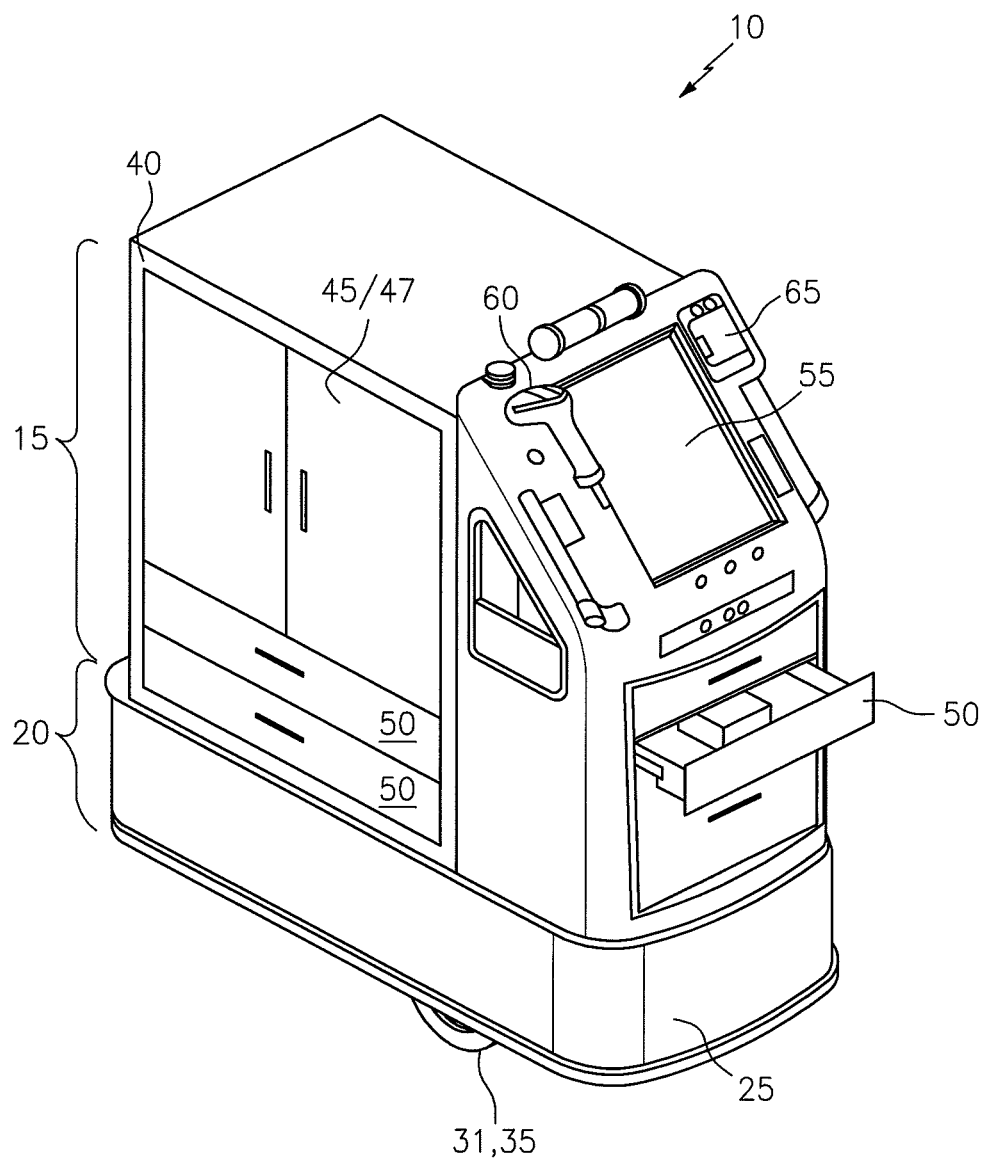
FIG. 1 schematically shows a robot that may implement illustrative embodiments of the invention.

Various embodiments of the present invention are described below with reference to the accompanying drawings. It should be understood that the following description is intended to describe exemplary embodiments of the invention, and not to limit the invention.

It is understood that the present invention is not limited to the particular components, analysis techniques, etc. described herein, as these may vary. It is also to be understood that the terminology used herein is used for the purpose of describing particular embodiments only, and is not intended to limit the scope of the present invention. It must be noted that as used herein, the singular forms "a," "an," and "the" include plural reference unless the context clearly dictates otherwise. The invention described herein is intended to describe one or more preferred embodiments for implementing the invention shown and described in the accompanying figures.

Unless defined otherwise, all technical and scientific terms used herein have the same meanings as commonly understood by one of ordinary skill in the art to which this invention belongs. Preferred methods, system components, and materials are described, although any methods and materials similar or equivalent to those described herein can be used in the practice or testing of the present invention.

Many modifications and variations may be made in the techniques and structures described and illustrated herein without departing from the spirit and scope of the present invention. Accordingly, the techniques and structures described and illustrated herein should be understood to be illustrative only and not limiting upon the scope of the present invention. The scope of the present invention is defined by the claims, which includes known equivalents and unforeseeable equivalents at the time of filing of this application In certain preferred embodiments of the present invention, the robot disclosed herein may be referred to as a "system" of components used in a hospital environment. For example, the robot may be used for transporting patient medications between wards, and cleaning up the waiting room when it has nothing else to do. One robot that may be used for these applications is the QCBOT robot, distributed by Vecna Technologies, Inc. of Cambridge, Mass. Of course, the robot may be used in various other applications, such as in a factory, a movie theater, or a consumer's home.

Other robots also can implement various embodiments. Accordingly, discussion of any specific type of robot, or its environment, is for illustrative purposes only and not intended to limit various embodiments and uses of the invention.

Illustrative embodiments relate specifically to autonomous robots operating without attendants (i.e., unattended robots) having a presence, either in person or remotely/virtually, in their local environments. Specifically, during normal use, the robots independently operate in their environment in some pre-defined/pre-specified manner without human guidance (i.e., autonomously). These robots also operate without requiring a person to be generally in their environment, either in person or remotely/virtually, managing or overseeing their movement and operation (i.e., unattended). For example, a robot may be programmed to clean a waiting room without an operator continually in the general vicinity/environment.

Many robots have a library of data relating to physical objects against which they compare physical objects they encounter in their environments. Accordingly, if an autonomous robot encounters a chair in a hospital waiting room, it searches its object library for an object having the visual characteristics of the chair, and then determines how to maneuver and operate in view of that chair. Problems arise, however, when a prior art autonomous robot encounters an object in its environment that is not in its object library. Often, such robots simply stop moving. An attendant in the environment can recognize this problem and correct it as needed. If unattended, however, the robot can sit idle indefinitely. To overcome this issue, illustrative embodiments provide the flexibility of detecting when an autonomous robot cannot resolve an object (i.e., when the robot cannot determine the identity of the object), and then controlling the robot to correctly move again without an attendant in the environment. Details are discussed below.

FIG. 1 schematically shows a robot 10 that may be implemented in accordance with illustrative embodiments of the invention. As shown, the robot 10 has a functional body 15 mounted on a mobility platform 20. Among other things, the mobility platform 20 includes a base 25 for mounting the body 15, and a drive structure 30 (not shown in detail) for moving the overall robot 10 in the desired manner around its environment. To that end, the drive structure 30 includes a plurality of wheels 35 mounted on an axle/motor structure. The drive structure 30 communicates with a central computing logic or controller to control its movement.

Additionally, as noted, the base 25 couples and supports various structures, such as the body 15. Those skilled in the art should recognize that the interchangeable nature of the types of bodies 15 that may couple with the base 25 are limited only by the desired application. In some embodiments, the base 25 also is capable of rotating 360 degrees. For example, the base 25 may rotate 360 degrees relative to the body 15, thus permitting the body 15 to remain in its current orientation. As another example, the base 25 and body 15 may rotate together.

The body 15 may include a wide variety of components depending on the application. In the embodiments shown, the body 15 includes a side panel 40 having a plurality of shelves 45 (covered in the figures by doors 47) and drawers 50 for transporting various items, and a front display/monitor 55 for controlling the robot 10 and communicating with its environment. For example, when used in the hospital context, the drawers 50 can contain medicine, patient charts, and small medical devices (e.g., syringes), while the shelves 45 can contain larger medical items, such as IV lines, fluid bags, and bed pans. Of course, other sides also can have shelves 45 and other storage areas, such as the front (as shown), back or opposite side and the drawers or the like can be locked and only accessible by the appropriate end user either manually or electronically.

The front display 55 may include a liquid crystal display device or other display device for communication purposes. In some embodiments, the display 55 is a touch screen display that enables a user to interact with internal robot logic. For example, the touch screen display 55 may display a keypad for a nurse to enter an ID, confirming receipt of medicine the robot 10 is carrying. Those skilled in the art can configure the touchscreen to have any of a wide variety of different functions depending on the application.

The front of the robot 10 also has various other components, such as a coupling device 60 for carrying items on its exterior (e.g., a thermometer), and an interface 65 for physically connecting with another device (e.g., via a USB port or a three-prong plug to energize an internal battery). Although not shown, the robot 10 also may have extension members that extend outwardly to grasp objects. For example, the robot 10 may have an anthropomorphic torso 30 and articulated arms 40 suited for lifting and carrying various payloads (e.g., medicine bottles).

The interior of the body 15 has an interior that houses logic controlling the movement and operation of the robot 10. Accordingly, the interior may include internal microprocessors, controllers, and other circuitry conventionally used for such purposes. In illustrative embodiments, visual, sound, inertial, special, and other sensors also are housed in the robot 10 collect data that enables the robot 10 to determine how and where to maneuver in its environment when in an autonomous mode. Data signals from these sensors, as well as data and control signals relative to positioning, orientation, etc., may be sent to and from a remote source to permit remote operation when in a manual mode (i.e., when an operator can control the robot 10). As discussed below with regard to FIG. 4, the data may be transmitted to and from the robot 10 using any communication media and technology known to those skilled in the art, via cables or other wired means or via wireless communications signals (e.g., Bluetooth, IR, etc.) across a network (e.g., a computer network, such as the Internet). In either case, transmitters and/or transponders, including Global Positioning System (GPS) units may be employed.

In accordance with at least one embodiment of the present invention, the robot 10 executes autonomous movements and behaviors based on vocal commands, e.g., "go bring that medicine bottle to room 200," or "clean the waiting room." In this specific embodiment, the vocal commands may be composed by invoking certain pre-recorded voice segments or, alternatively, by using a voice-recognition system that translates the vocal commands into programmatic instructions for execution by the robot 10. As previously discussed, these instructions may be conveyed to the robot 10 via wired or wireless communication signaling technology, or by an operator in the environment. These and other signals/messages may be transmitted via an interface (e.g., a microphone, RF receiver, or USB port on the outer portion of the body 15), which can be formed from a single hardware port, or a plurality of hardware ports (e.g., a first hardware port for incoming signals, and a second hardware port for outgoing signals) on the robot 10. Other embodiments pre-program the robot 10 to perform specific or general tasks without voice commands.

In addition to assisting with movement of the entire robot 10, various embodiments also facilitate movement of specific portions of the robot 10. For example, the robot 10 may not be able to resolve the identity of a type of medicine bottle it is to grasp. Accordingly, illustrative embodiments may control the noted extending members to move in an appropriate manner to grasp the medicine bottle without dropping or damaging the bottle.

The control architecture is highly flexible. For example, when in a manual mode, the robot 10 may use an operator control unit that features joysticks and other standard user interface components. Other embodiments may employ Artificial Intelligence (AI) systems to enable the robot 10 to navigate, avoid obstacles, learn from human users and interact with users in socially appropriate ways.

Additionally, as noted above, the platform could be used in other commercial and consumer applications. For example, the robot's capabilities can be extended to include assisting elderly, disabled or otherwise-incapacitated users with Activities of Daily Living ("ADLs") with complete safety. ADLs include getting in and out of bed, getting in and out of a bathtub, getting on and off the toilet, and generally navigating around the disabled user's living quarters.

As discussed above, the robotic platform of FIG. 1 is but one type of robot that may implement illustrative embodiments. Other robot platforms can implement various embodiments. Accordingly, detailed discussion of the platform is for exemplary purposes and not intended to limit various embodiments of the invention.

In illustrative embodiments, the robot 10 is similar to the robot disclosed in co-pending, co-owned U.S. patent application Ser. No. 13/872,362, filed on Apr. 29, 2013, and entitled, "Mobile Robot for Receiving, Transporting, and/or Delivering One or More Pharmaceutical Items," the disclosure of which is incorporated herein, in its entirety, by reference.

Figure 2:
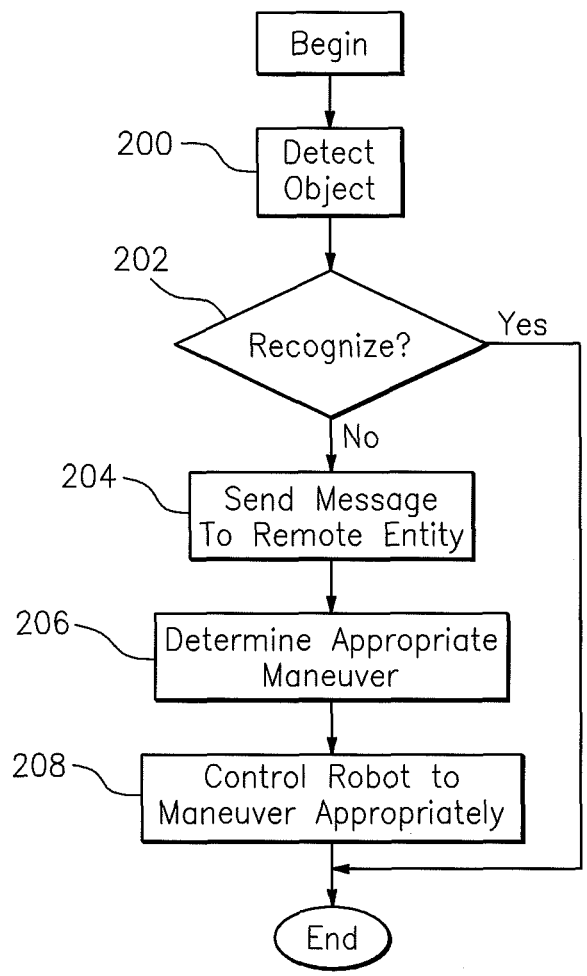
FIG. 2 shows a process of assisting a robot in accordance with illustrative embodiments of the invention.

FIG. 2 shows a process of assisting the movement of an autonomous, unattended robot 10, such as the robot 10 in FIG. 1, in accordance with illustrative embodiments of the invention. This process is a simplified version of what could be a much longer process. Accordingly, the process may entail additional steps that are not discussed in FIG. 2. Moreover, some embodiments may perform various steps in a different order than that described. Those skilled in the art should be able to make appropriate changes to the order and number of steps in the process, and still meet the spirit of various embodiments.

Figure 3:
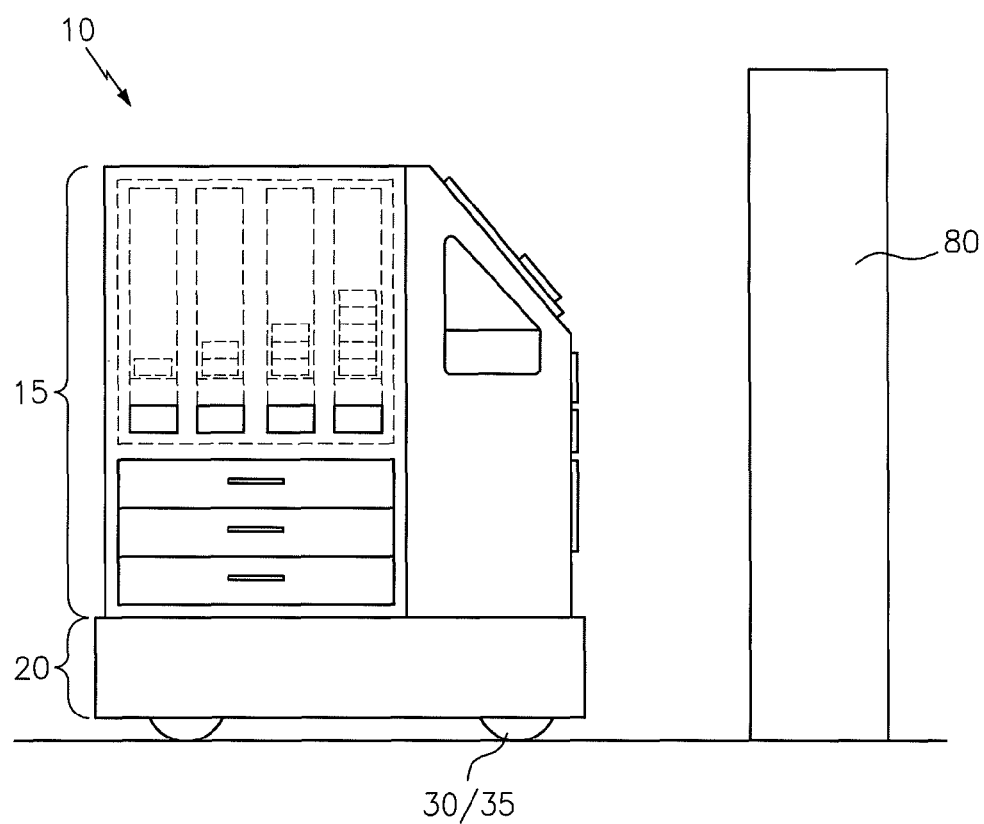
FIG. 3 schematically shows a robot interacting with an object in its environment in accordance with illustrative embodiments of the invention.

The process of FIG. 2 can be executed simultaneously in connection with one or a plurality of autonomous, unattended robots 10 operating in the same or different environments. The process begins at step 200, in which the robot 10 detects an object 80 in its environment. For example, see FIG. 3, which shows the robot 10 encountering a generic object 80 and its environment. Of course, the object 80 may be any of a number of different things that affect movement of part or all of the robot 10. For example, in a hospital environment, the object 80 may be something supported on the floor, such as a chair or IV pole, or something supported by another object 80, such as a thermometer or a medicine bottle on a table. The robot 10 is configured to make some kind of movement in response to the object 80.

To that end, a controller or other logic (e.g., within the robot 10) determines if it can recognize the object 80 (step 202). For example, the robot 10 may access local or remote memory having a library of objects 80, and corresponding predefined actions or responses to the object 80. Accordingly, if the robot 10 recognizes that the object 80 is a chair in its path of movement, then control logic may cause the robot 10 to maneuver around the chair. As a second example, if the robot 10 recognizes that the object 80 is a medicine bottle, and it is programmed to grasp the medicine bottle, then its robotic arm 40 may reach out and grasp the medicine bottle, which would end the process.

If the controller does not recognize the object 80, however, then its movement may be impeded—its movement may be fully stopped or substantially slowed. For example, the robot 10 may not have the ability to maneuver past the object 80, or may move inefficiently past the object 80. In that case, the process continues to step 204, in which the controller initiates and/or forwards a help message to a remote entity 82 (see FIG. 4, discussed below) via a data transmission interface on the robot 10. In illustrative embodiments, the remote entity 82 plays the role of a "help center" that assists one or more robots 9 that are "stuck," i.e., robots 9 that cannot recognize objects 80 in their environments and are unable to make a next appropriate maneuver/motion as intended.

To that end, the robot 10 may have a transmitter that transmits one or more help messages across a network 84 to one or more remote entity/help centers 82. These help messages may include a modest amount of data (e.g., just enough to notify the remote entity 82 that there is a problem). In other embodiments, these help messages are rich with data about the environment. For example, the help message may include robot identification data and environmental data obtained via its many sensors.

Figure 4:
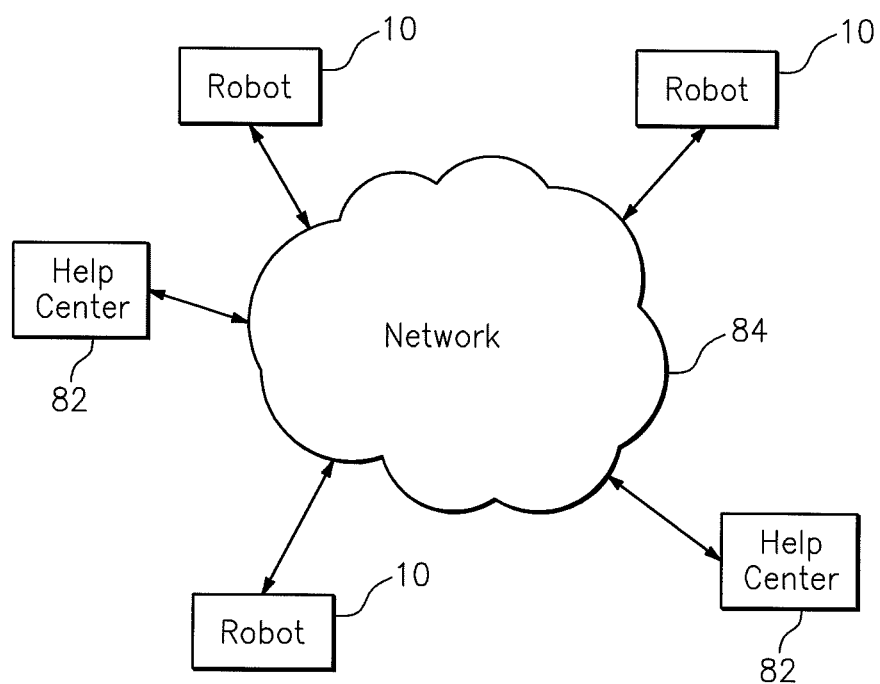
FIG. 4 schematically shows a network for communicating between a robot and a help center in accordance with illustrative embodiments of the invention.

As noted, the remote help center 82 illustratively is not in the same environment as the robot 10. For example, the help center 82 may be a) in another room or portion of the same building (i.e., a separate part that cannot see or hear the robot 10), b) in the same campus, c) miles away but in the same general vicinity or city, d) in another part of the same country, or e) in another country on the same continent or on the other side of the world. Some help centers 82 may be portable and not permanently within a building or edifice (e.g., a support person's smartphone). In illustrative embodiments, the remote entity/help/call center 82 may be implemented at least in part on a computer device 88 (FIG. 5), such as a laptop computer, desktop computer, server, high-performance computer device, tablet, or smartphone. Some embodiments simply implement the remote entity 82 as another robot 10. As discussed below, a person or machine logic (e.g., artificial intelligence) at the remote entity 82 may coordinate the appropriate response. Crowd-sourcing resources also may act to coordinate an appropriate response FIG. 4 schematically shows a network that can provide these services to multiple robots 9 simultaneously, or to a single robot. As shown, the network may have multiple help centers 82 that each assist different sets of one or more robots 9 through a larger network 84, such as the Internet or a virtual private network (VPN). In addition or alternatively, each robot 10 may be assigned to two or more help centers 82 that act as redundant support. Specifically, in that case, if the first help center 82 is busy or unable to rapidly assist, then the robot 10 may direct their help request to another help center 82 that is not busy. This redundancy should help balance the load across the network 84 and provide faster response times.

Figure 5:
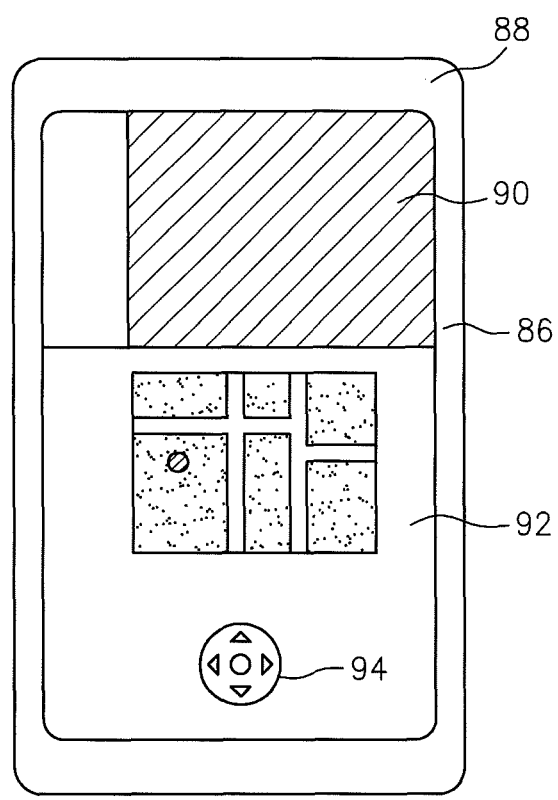
FIG. 5 schematically shows a portable computing device in a graphical user interface that may be used in accordance with illustrative embodiments of the invention.

After receiving the help message, the remote entity 82 (or the robot 10 with assistance from the help center 82) determines an appropriate maneuver for the robot 10 to make in view of the object 80 (step 206). To assist with that determination, illustrative embodiments may display details of the environment to the remote entity 82. FIG. 5 schematically shows one example of a graphical user interface 86 on a computer device 88, such as a tablet or smart phone, that helps a person making that determination. As shown, the computer device graphical user interface 86 has a top panel 90 showing the view from the front of the robot 10, and a bottom panel 92 showing the position of the robot 10 within its environment. In this example, the bottom panel 92 shows that the robot 10 is stuck against a wall, but has an opening to the left through which it can move. The top panel 90 shows the wall and its edge through a video feed or picture. Accordingly, in this example, the remote entity 82 should forward control signals or other information to the robot 10, enabling it to maneuver around the edge of the wall.

Of course, those skilled in the art can have many other features on the graphical user interface 86, such as indicia showing the identity of the robot 10, and indicia for showing other environmental features. Moreover, the computer device 88 can act as another type of interface, such as a sound interface that receives and transmits sound to/from the robot. Accordingly, a graphical user interface 86, such as that shown in FIG. 5, is but one example of any of a wide variety of user interfaces that may cooperate with illustrative embodiments.

Other embodiments may use machine learning engines and artificial intelligence processes to determine an appropriate maneuver for the robot 10. For example, if a certain problem occurs some predetermined number of times, then correction logic at the remote entity 82, the robot 10, or some other location, can record the corrected action and store that action in a database for future reference. Accordingly, before requiring a person to review the situation, the remote entity 82 (or robot) may access this database to determine if there is precedent for this problem and an appropriate response.

Accordingly, the process concludes at step 208, in which the noted control signals are forwarded and processed by the robot 10, which enables the robot 10 to maneuver appropriately in view of the object 80. In the example shown, the control signals include movement information that enables the robot 10 to maneuver around the edge of the wall. The solution may be stored in the machine learning engine database for future use.

Any number of different techniques can generate and transmit the control signals that move the robot 10 past its impediment. In the embodiment shown in FIG. 9, the computer device 88 has graphical indicia showing arrows that effectively form a joystick 94 for remotely controlling the robot 10. Accordingly, the user may manipulate the joystick 94 to appropriately move the robot 10. Of course, other means may be used to control the robot 10, and the joystick 94 is but one example. Another example may simply use the inertial sensors resident on the computer device 88 (e.g., accelerometers or gyroscopes on a smartphone) to maneuver the robot 10. Other embodiments may have other means for controlling just a part of the robot 10, such as an arm 40 or hand 50.

In illustrative embodiments, the robots 9 are configured to operate at least in an autonomous mode or in a manual mode. Accordingly, to enable the help center 82 to maneuver the robot 10, illustrative embodiments first move the robot 10 into a manual mode, and then maneuver the robot 10 as needed through its impediment. After the robot 10 is clear of the obstacle and no longer has impeded movement, then the robot 10 may be shifted back to its autonomous mode.

In illustrative embodiments, this complete process of FIG. 2 can be performed quickly and generally transparently from the perspective of its environment. For example, a person sitting in the waiting room while the robot 10 is cleaning likely will not notice or recognize any more than a negligible delay or change of movement of the robot 10 during this process.

Accordingly, illustrative embodiments free attendants from generally continuously monitoring autonomous robots—either locally or remotely. Instead, people now can be located remotely and assist with impediments on an as-needed basis. This reduced time demand favorably enables a single person to more efficiently assist dozens of robots in disparate and remote environments.

Various embodiments of the invention may be implemented at least in part in any conventional computer programming language. For example, some embodiments may be implemented in a procedural programming language (e.g., "C"), or in an object oriented programming language (e.g., "C++"). Other embodiments of the invention may be implemented as preprogrammed hardware elements (e.g., application specific integrated circuits, FPGAs, and digital signal processors), or other related components.

In an alternative embodiment, the disclosed apparatus and methods (e.g., see the various flow charts described above) may be implemented at least in part as a computer program product for use with a computer system. Such implementation may include a series of computer instructions fixed either on a tangible, non-transitory medium, such as a computer readable medium (e.g., a diskette, CD-ROM, ROM, or fixed disk). The series of computer instructions can embody all or part of the functionality previously described herein with respect to the system.

Those skilled in the art should appreciate that such computer instructions can be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies.

Among other ways, such a computer program product may be distributed as a removable medium with accompanying printed or electronic documentation (e.g., shrink wrapped software), preloaded with a computer system (e.g., on system ROM or fixed disk), or distributed from a server or other remove device over the network (e.g., the Internet or World Wide Web). Of course, some embodiments of the invention may be implemented as a combination of both software (e.g., a computer program product) and hardware. Still other embodiments of the invention are implemented as entirely hardware, or entirely software.

Although the description above contains many specific examples, these should not be construed as limiting the scope of the embodiments of the present disclosure but as merely providing illustrations of some of the presently preferred embodiments of this disclosure. Thus, the scope of the embodiments of the disclosure should be determined by the appended claims and their legal equivalents, rather than by the examples given.

It will be appreciated by those skilled in the art that changes could be made to the embodiments described above without departing from the broad inventive concept thereof. It is understood, therefore, that this disclosure is not limited to the particular embodiments disclosed, but it is intended to cover modifications within the spirit and scope of the embodiments of the present disclosure.

What is claimed is:

1. A robot controller apparatus comprising:
    an input port for receiving a first message from an unattended robot relating to movement of the robot, receipt of the first message indicating that movement of the robot is impeded by a non-human object;
    a movement controller operatively coupled with the input port, the movement controller being configured to determine how to correct the impeded movement caused by the non-human object; and
    an output port operatively coupled with the movement controller, the output port being configured to forward a second message toward the robot having correction information that enables the robot to move without impediment by the non-human object.

2. The robot controller apparatus as defined by claim 1 wherein the input port and output port comprise a single hardware or software interface.

3. The robot controller apparatus as defined by claim 1 wherein the movement controller includes a visual display for displaying visual indicia showing the environment of the robot.

4. The robot controller apparatus as defined by claim 1 wherein the movement includes movement of at least a portion of the entire robot relative to its environment.

5. The robot controller apparatus as defined by claim 1 wherein the robot has an autonomous mode and a manual mode, further wherein the output port is configured to forward control commands toward the robot to control movement of the robot when in the manual mode.

6. The robot controller apparatus as defined by claim 1 wherein the non-human object is an inanimate object.

* * * * *